US00PP11529P

United States Patent [19]

Ferrer

[11] Patent Number: Plant 11,529

[45] Date of Patent: Sep. 26, 2000

[54] HYBRID TEA ROSE PLANT NAMED 'FEBESA'

[75] Inventor: Matilde Ferrer, Valencia, Spain

[73] Assignee: CP (Delaware), Inc., Wilmington, Del.

[21] Appl. No.: 09/150,089

[22] Filed: Sep. 9, 1998

[51] Int. Cl.[7] ..... A01H 5/00

[52] U.S. Cl. ..... Plt./137

[58] Field of Search ..... Plt./135, 137, 130

*Primary Examiner*—Howard J. Locker

*Attorney, Agent, or Firm*—Burns, Doane, Swecker & Mathis, L.L.P.

[57] ABSTRACT

A new and distinct variety of Hybrid Tea rose plant is provided which abundantly forms attractive blossoms which are stable light pink in coloration and very clean in appearance. The buds are large, and are borne on straight erect stems. Attractive semi-glossy medium green foliage is formed. The new variety is particularly well suited for forming cut flowers on a highly productive basis under greenhouse growing conditions.

1 Drawing Sheet

SUMMARY OF THE INVENTION

The new variety of *Rosa hybrida* Hybrid Tea rose plant was created by artificial pollination wherein two parents were crossed which previously had been studied in the hope that they would contribute the desired characteristics. The female parent (i.e., the seed parent) of the new variety was an unnamed seedling (non-patented in the United States). The male parent (i.e., the pollen parent) was the 'Lambada' variety (non-patented in the United States). The parentage of the new variety can be summarized as follows:

Unnamed Seedling×'Lambada'.

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characteristics:

(a) forms attractive large buds on straight erect stems,
(b) forms in abundance attractive blossoms which are stable light pink in coloration and very clean in appearance,
(c) forms attractive semi-glossy medium green foliage, and
(d) is particularly well suited for the production of cut flowers under greenhouse growing conditions.

The new variety readily can be distinguished from its 'Lambda' parent variety. More specifally, the blossom coloration of the 'Lambda' variety is near orange unlike that of the new variety of the present invention.

The new variety well meets the needs of the horticultural industry and exhibits good productivity during cut flower production in a greenhouse. Good tolerance to powdery mildew is exhibited.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Febesa' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during April while budded on *Rosa indica* understock and growing in greenhouses at Le Cannet des Maures, Var, France. Dimensions in centimeters are indicated at the bottom of the photograph. Page No. 37 from the R.H.S. Colour Chart of The Royal Horticultural Society is shown at the lower-left portion of the photograph for comparative purposes since it illustrates a very similar coloration.

FIG. 5 illustrates a specimen of a flower in the course of opening;

DETAILED DESCRIPTION

Figures 1, 2, 3, 4, 6, 7, 8, 9, 10, 11, 12, 13, 14, 15, 16:
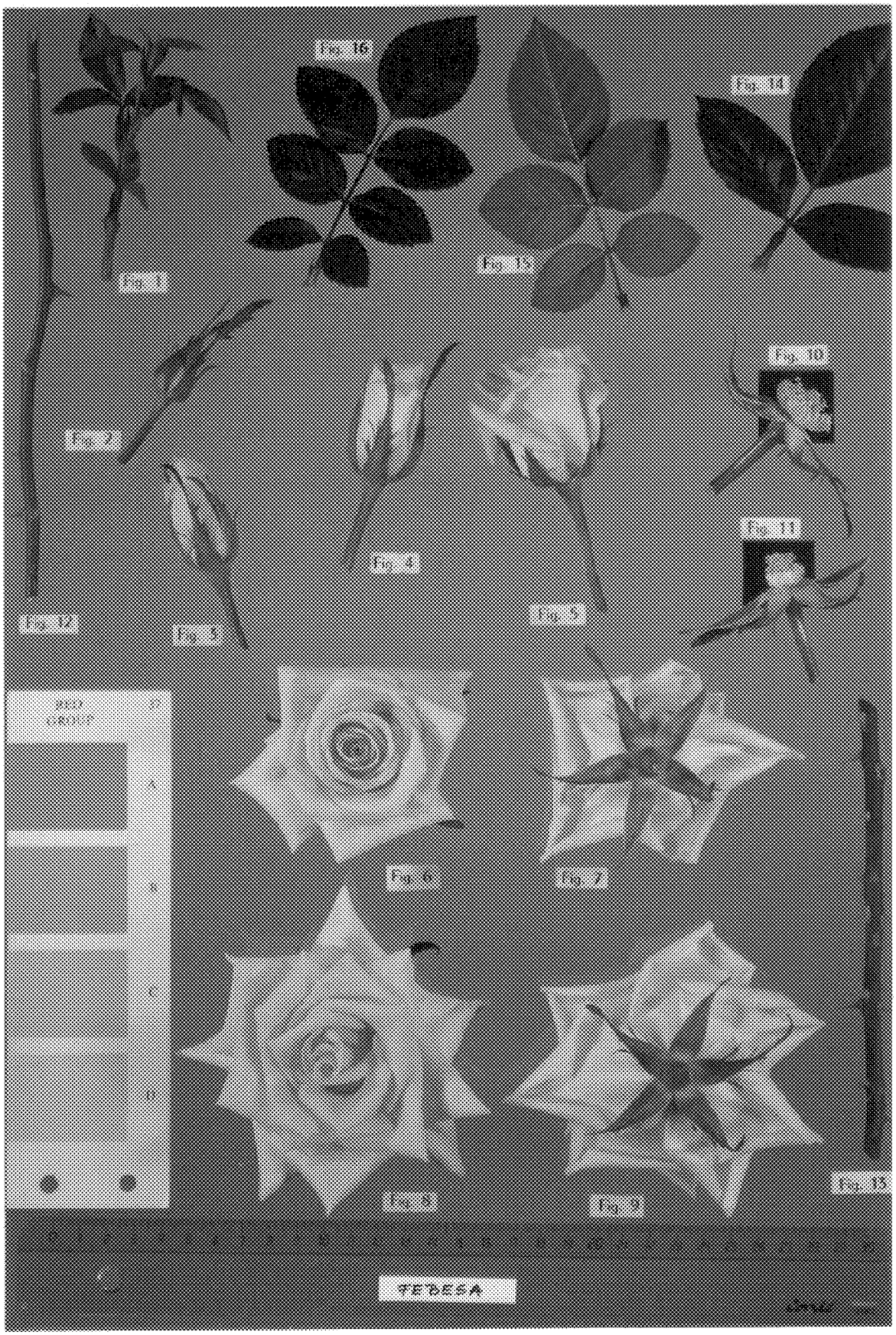
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 6 illustrates a specimen of an open flower—plan view—obverse.
FIG. 7 illustrates a specimen of an open flower—plan view—reverse.
FIG. 8 illustrates a specimen of a fully open flower—plan view—obverse.
FIG. 9 illustrates a specimen of a fully open flower—plan view—reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates a specimen of a leaf with three leaflets—plan view—upper surface.
FIG. 15 illustrates a specimen of a leaf with five leaflets—plan view—under surface.
FIG. 16 illustrates a specimen of leaf with seven leaflets—plan view—upper surface.

The chart used in the identification of the colors is that of The Royal Horticultural Society (R.H.S. Colour Chart). The description is based on the observation of two year-old plants during May while budded on *Rosa indica* understock and growing indoors at Le Cannet des Maures, Var, France. The coloration in common terms precedes reference to the chart in some instances.

Class: Hybrid tea.

Plant:

*Height.*—When pruned to a height of 85 cm., floral stems of approximately 50 to 80 cm. in length commonly are produced.

*Habit.*—Erect.

Branches:

*Color.*—Young stems: Yellow-Green Group 146A in coloration. Adult wood: Green Group 137A in coloration.

*Thorns.*—Size: Medium (as illustrated). Quantity: Numerous. Color: Near Greyed-Orange Group 167A (as illustrated).

Leaves:

*Stipules.*—Adnate, and pectinate.

*Petioles.*—Upper surface: Medium green (near Yellow-Green Group 147A to 147D) and somewhat glandular. Under surface: Medium green with numerous prickles.

*Leaflets.*—Number: 3, 5, and 7 (most often). Shape: Elliptic. Size: Medium. Serration: Regular (as illustrated). Texture: Somewhat consistent. General appearance: Very dense, medium green, and semi-glossy. Color (young foliate): Upper surface: Yellow-Green Group 147A with some reddish staining. Under surface: Yellow-Green Group 147B with some reddish staining. Color (adult foliage): Upper surface: Green Group 139A. Under surface: Green Group 138A.

Inflorescence:

*Number of flowers.*—Usually one flower per stem.

*Peduncle.*—Light green (near Green Group 138D) in coloration, and the length is approximately 8.5 cm. on average. Commonly turns towards the dominant light source.

*Sepals.*—Upper surface: Greenish (near Green Group 137D) in coloration. Under surface: Lighter green with some heavily foliated extensions (as illustrated).

*Buds.*—Shape: Elongated. Size: Large. Length: Approximately 5.5 cm. on average. Color upon opening: Upper surface: Orient Pink, Red Group 36A. Under surface: Dawn Pink, Red Group 49D.

*Flower.*—Shape: Commonly with a high center. Diameter: Commonly approximately 9 cm. on average. Petal number: Approximately 23 on average. Color (when opening begins): Upper surface: Orient Pink, Red Group 36C with some Red Group 38B at the margin. Under surface: Orient Pink, Red Group 36D. Color (when blooming): Upper surface: Orient Pink, Red Group 36B with some Red Group 39D at the margin. Under surface: Orient Pink, Red Group 36D. Color (at end of opening): Upper surface: Orange Group 29D. Under surface: Orange-White Group 159B. Fragrance: None. Lasting quality: Good. The blossoms commonly last approximately 10 days on the plant and approximately 9 to 11 days when cut and placed in a vase. Petal shape: Rounded with an obtuse base, and reflexed edges with some quilling. Petal drop: Good, the petals commonly detach cleanly. Stamen number: Approximately 106 on average. Anthers: Ochre in coloration. Filaments: Yellowish in coloration. Pollen: Present. Pistils: Approximately 146 on average. Stigmas: Yellow-strawlike in coloration. Styles: Light pink in coloration. Receptacle: Light green in coloration, smooth, and in longitudinal section in the shape of a funnel. Productivity: Commonly yields approximately 160 to 220 blossoms per square meter per year under greenhouse growing conditions.

I claim:

1. A new and distinct variety of Hybrid Tea rose plant characterized by the following combination of characteristics:

(a) forms attractive large buds on straight erect stems,
(b) forms in abundance attractive blossoms which are stable light pink in coloration and very clean in appearance,
(c) forms attractive semi-glossy medium green foliage, and
(d) is particularly well suited for the production of cut flowers under greenhouse growing conditions;

subtantially as herein shown and described.

* * * * *

PRO
LRULE

TEDESA